United States Patent
Kirsch

(10) Patent No.: US 8,833,549 B2
(45) Date of Patent: *Sep. 16, 2014

(54) ENDOSTITCH PACKAGES

(71) Applicant: Covidien LP, Mansfield, MA (US)

(72) Inventor: David Kirsch, Madison, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/046,140

(22) Filed: Oct. 4, 2013

(65) Prior Publication Data

US 2014/0021069 A1  Jan. 23, 2014

Related U.S. Application Data

(63) Continuation of application No. 13/473,928, filed on May 17, 2012, now Pat. No. 8,556,069, which is a continuation of application No. 12/544,779, filed on Aug. 20, 2009, now Pat. No. 8,196,739.

(51) Int. Cl.
*A61B 17/06* (2006.01)

(52) U.S. Cl.
USPC ............... 206/63.3; 206/339; 206/380

(58) Field of Classification Search
CPC ... A61B 17/06; A61B 17/06114; B65D 85/24
USPC ......... 206/63.3, 380, 388, 49, 574, 227, 229, 206/213, 304.2, 363, 364, 210, 239, 337, 206/365, 382, 370, 339; 606/228, 148; 242/159; 132/324, 327; 604/171, 174; 220/254.3, 254.1, 254.7
See application file for complete search history.

(56) References Cited

U.S. PATENT DOCUMENTS

| | | |
|---|---|---|
| 2,615,565 A | 10/1952 | Bower et al. |
| 3,495,703 A | 2/1970 | Calabrese |
| 3,972,418 A | 8/1976 | Schuler et al. |
| 4,424,898 A | 1/1984 | Thyen et al. |
| 4,572,363 A | 2/1986 | Alpern |
| 4,961,498 A * | 10/1990 | Kalinski et al. ............... 206/339 |
| 4,967,902 A | 11/1990 | Sobel et al. |
| 5,052,551 A | 10/1991 | Cerwin et al. |
| 5,056,658 A | 10/1991 | Sobel et al. |
| 5,154,283 A | 10/1992 | Brown |
| 5,165,217 A | 11/1992 | Sobel et al. |
| 5,213,210 A | 5/1993 | Cascio et al. |
| 5,228,565 A | 7/1993 | Sinn |
| 5,230,424 A | 7/1993 | Alpern et al. |
| 5,236,083 A | 8/1993 | Sobel et al. |

(Continued)

OTHER PUBLICATIONS

European Search Report for EP 10 25 1467 date of completion is Oct. 13, 2010 (3 pages).

*Primary Examiner* — Luan K Bui
*Assistant Examiner* — Rafael Ortiz

(57) ABSTRACT

A suture package assembly is provided and includes a suture tray having a loading unit mounted thereon for supplying a surgical needle-suture assembly to a surgical instrument. A suture package cover is provided to protect the surgical needle-suture assembly prior to use. The suture package cover includes a disc engagable with the suture tray to protect the suture retained in the suture tray and an elongate flap configured to overlie the loading unit to protect the surgical needle contained therein. The elongate flap is bendable relative to the disk along a primary fold line and includes a nose portion removably engagable with the disk.

16 Claims, 11 Drawing Sheets

(56) References Cited

U.S. PATENT DOCUMENTS

| | | | |
|---|---|---|---|
| 5,249,671 | A | 10/1993 | Sinn |
| 5,249,673 | A | 10/1993 | Sinn |
| 5,271,495 | A | 12/1993 | Alpern |
| 5,284,240 | A | 2/1994 | Alpern et al. |
| 5,301,801 | A | 4/1994 | Sinn |
| 5,350,060 | A | 9/1994 | Alpern et al. |
| 5,392,903 | A | 2/1995 | Sinn |
| 5,462,162 | A | 10/1995 | Kaplan et al. |
| 5,472,081 | A | 12/1995 | Kilgrow et al. |
| 5,478,344 | A | 12/1995 | Stone et al. |
| 5,478,345 | A * | 12/1995 | Stone et al. ............ 606/144 |
| 5,503,266 | A | 4/1996 | Kalbfeld et al. |
| 5,533,611 | A | 7/1996 | Bordighon et al. |
| D374,284 | S | 10/1996 | Stone et al. |
| D374,285 | S | 10/1996 | DeFonzo et al. |
| 5,575,382 | A | 11/1996 | Sobel et al. |
| D378,131 | S | 2/1997 | Stone et al. |
| 5,615,766 | A | 4/1997 | Gemma et al. |
| 5,628,395 | A | 5/1997 | Daniele et al. |
| 5,655,652 | A | 8/1997 | Sobel et al. |
| 5,667,155 | A | 9/1997 | Cerwin et al. |
| 5,669,490 | A | 9/1997 | Colligan et al. |
| 5,728,107 | A | 3/1998 | Zlock et al. |
| 5,733,293 | A | 3/1998 | Scirica et al. |
| 5,755,729 | A | 5/1998 | De la Torre et al. |
| 5,769,214 | A | 6/1998 | Zatarga |
| 5,819,918 | A | 10/1998 | Scanlon |
| 5,833,055 | A | 11/1998 | Cerwin et al. |
| 5,887,706 | A | 3/1999 | Pohle et al. |
| 5,906,273 | A | 5/1999 | Pohle et al. |
| 6,047,815 | A * | 4/2000 | Cerwin et al. ............ 206/63.3 |
| 6,076,659 | A | 6/2000 | Baumgartner et al. |
| 6,098,796 | A | 8/2000 | Januzeli et al. |
| 6,135,272 | A | 10/2000 | Sobel et al. |
| 6,260,699 | B1 | 7/2001 | Kaplan et al. |
| 6,464,071 | B2 | 10/2002 | Baumgartner |
| 6,481,568 | B1 | 11/2002 | Cerwin et al. |
| 6,533,112 | B2 | 3/2003 | Warnecke |
| 6,644,469 | B2 | 11/2003 | Alpern |
| 2004/0050721 | A1 | 3/2004 | Roby et al. |
| 2005/0035007 | A1 | 2/2005 | Kennedy et al. |
| 2006/0226031 | A1 | 10/2006 | Kennedy et al. |
| 2007/0227914 | A1 | 10/2007 | Cerwin et al. |
| 2007/0256945 | A1 | 11/2007 | Kennedy et al. |
| 2008/0185752 | A1 | 8/2008 | Cerwin et al. |
| 2009/0205987 | A1 | 8/2009 | Kennedy et al. |
| 2009/0250356 | A1 | 10/2009 | Kirsch et al. |
| 2010/0084294 | A1 | 4/2010 | Kirsch et al. |
| 2010/0147708 | A1 * | 6/2010 | McHugh Karow et al. . 206/63.3 |
| 2011/0056859 | A1 * | 3/2011 | Kozlowski ............ 206/370 |

\* cited by examiner

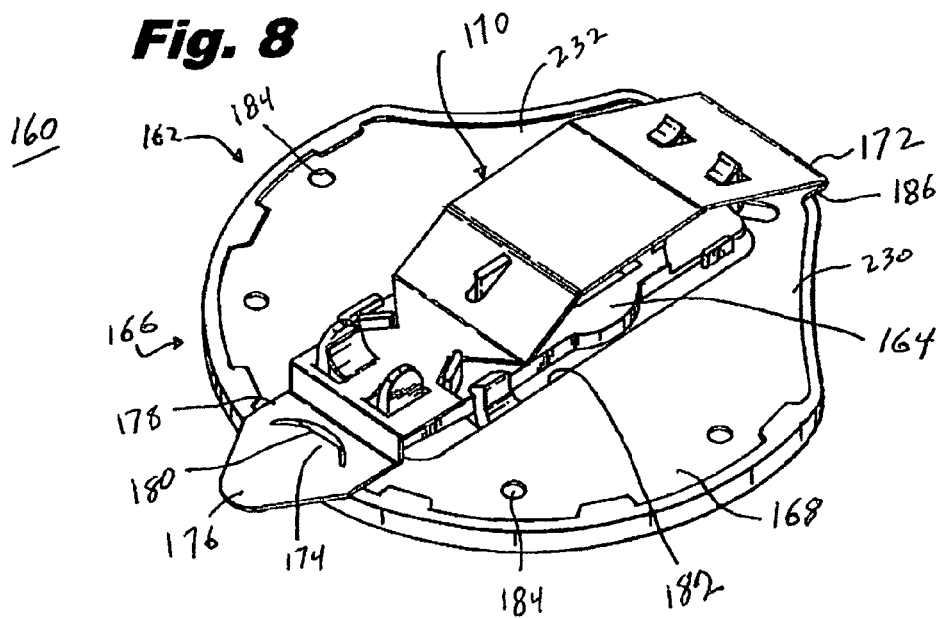
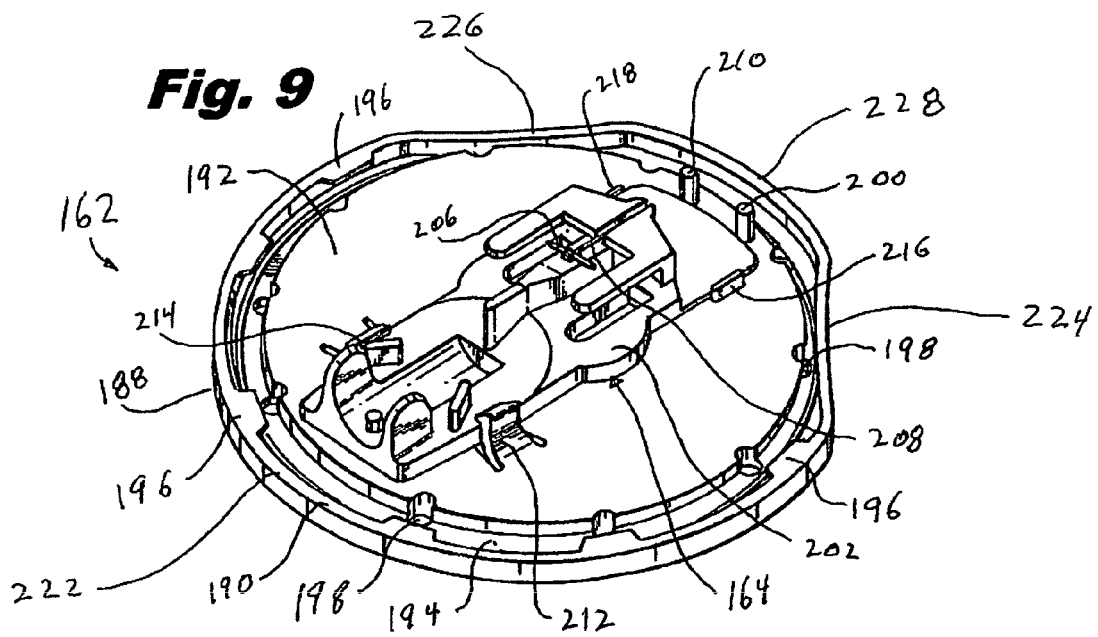

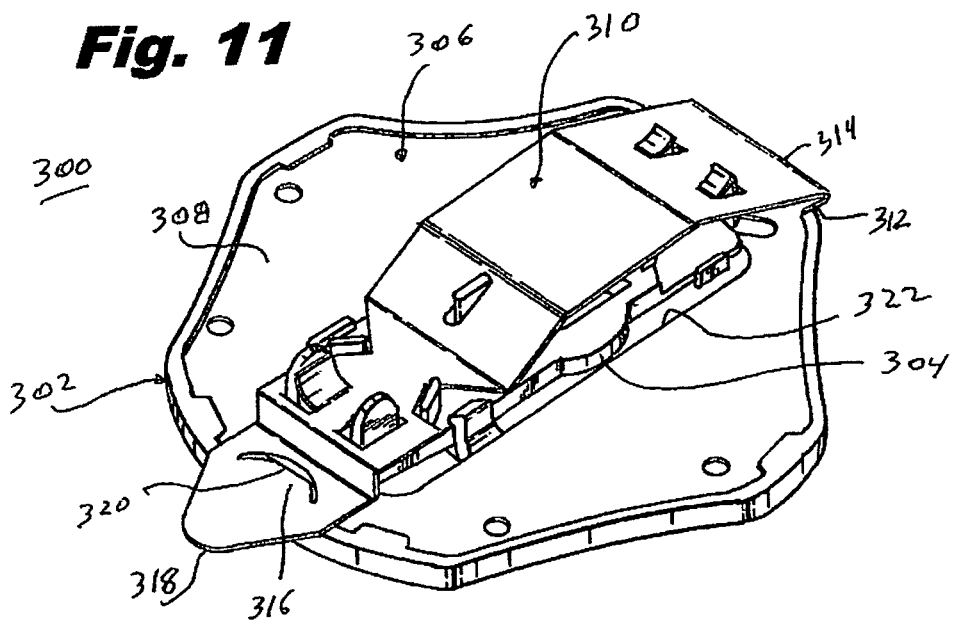
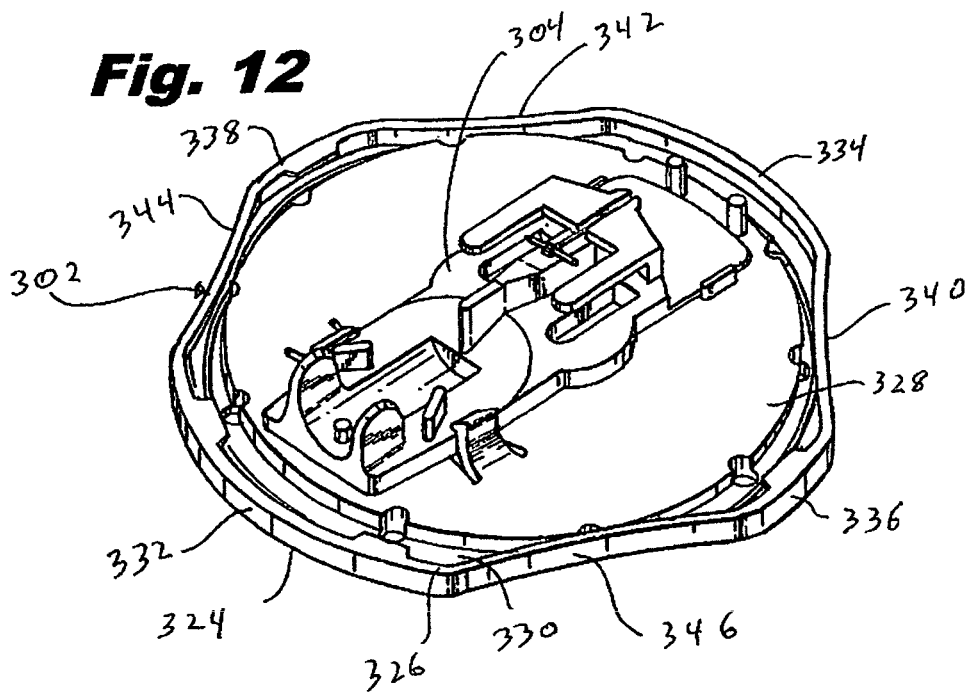

ENDOSTITCH PACKAGES

CROSS-REFEERENCE TO RELATED APPLICATIONS

This application is a continuation of U.S. application Ser. No. 13/473,928 filed May 17, 2012, now patented U.S. Pat. No. 8,556,069, which is a continuation of U.S. application Ser. No. 12/544,779 filed Aug. 20, 2009, now U.S. Pat. No. 8,196,739, the entire discloure if which is incorporated by reference herein.

BACKGROUND

1. Technical Field

The present disclosure relates to suture packages for supplying a surgical needle, and more specifically, an endostitch needle, having a length of suture material attached thereto. More particularly, the present disclosure relates to a suture package having a circular body portion defining a suture tray for receipt of the length of suture material, a loading unit affixed to the circular body portion for supporting the surgical needle, and a cover to protect the needle and suture prior to use.

2. Background of Related Art

During various surgical procedures it is often necessary to manipulate a surgical needle, having a length of suture material attached thereto, with a surgical suturing apparatus. This is particularly true in minimally invasive surgical procedures wherein the surgery is performed through a small incision or port allowing access to a body cavity.

Various forms of packaging or devices have been developed to provide the surgical needle and an associated length of suture material to the surgical suturing apparatus. These packages or devices typically hold the surgical needle loosely within the packaging and bend or wrap the length of suture material within the packaging to conserve space. The length of suture material may be wrapped into a figure eight configuration. Alternatively, the length of suture material may be wrapped around a spool positioned within the packaging.

In a particular application, a double-ended surgical needle is used in conjunction with the surgical suturing apparatus. The double-ended surgical needle is alternately secured within the jaws of the surgical suturing apparatus, specifically within small holes formed within the jaws. In order to load the surgical needle within the jaws of the suturing apparatus, the jaws of the suturing apparatus and, specifically, the holes formed therein, must be precisely aligned over opposite ends of the double ended surgical needle.

Additionally, some surgical procedures are best performed with the use of a barbed length of suture material having a loop at one end thereof. After suturing the appropriate tissue, the surgical needle is passed through the loop such that the barbs in the length of suture material engage the interior of the loop to lock the suture in place about the tissue. Due to the presence of barbs, which tend to engage or foul with each other, it is often not possible to wrap a length of suture material within compact packaging such that it passes back over itself.

Furthermore, the needle's position on a loading unit is critical to the needle being able to be received in the jaws of the surgical suturing apparatus.

Therefore, a need exists for a suture package assembly which is capable of precisely positioning a surgical needle for receipt by a surgical suturing apparatus. There is also a need for a suture package assembly having a cover to protect the surgical needle and length of suture material prior to use.

SUMMARY

There is disclosed a suture package assembly including a suture tray having a body portion with a peripheral rim and a central body portion defining a circumferential suture retaining trough therebetween. A loading unit is attached to a central body portion of the suture tray. A cover is engageable with the body portion and includes a circular disk having a cut out for receipt of the loading unit therethrough and an elongate flap extending from the circular disk. The circular disk is positioned over the suture tray and the elongate flap is folded relative to the circular disk along a primary fold line such that the elongate flap covers the loading unit. The suture tray includes a plurality of inwardly directed tabs along the peripheral rim which are engageable with the disk to retain the disk on the suture tray.

The elongate flap terminates in a nose having a tab and the circular disk includes a slot such that the tab engages the slot to secure the elongate flap over the loading unit.

In a specific embodiment, the loading unit is removably attached to the body portion.

There is also disclosed a cover, for use with a suture tray having a loading unit mounted thereon, including a disk having cut out for receipt of the loading unit and an elongate flap extending from the disk. The elongate flap includes a plurality of panels separated by fold lines. A first end of the elongate flap is connected to the disk along a primary fold line. The disk includes a slot and a second end of the elongate flap is engageable within the slot to secure the elongate flap to the disk. In one embodiment, the disk is a substantially circular disk.

In an alternative embodiment, the disk includes alternating arcuate and scalloped peripheral portions.

There is also disclosed a method of covering a suture tray and a loading unit positioned on the suture tray including providing a cover having a disk and an elongate flap extending from one peripheral side edge of the disk. The cover has a first side including a disk first side and a flap first side. The method includes the step of positioning the disk over the suture tray such that the disk covers a suture positioned in the suture tray and folding the elongate flap along a first fold line such that the disk first side is adjacent to the flap first side.

The method further includes the step of securing a nose end of the flap to a second peripherals side edge of the disk opposite a first peripheral side edge of the disk.

The method additionally includes the step of folding the elongate flap such that a portion of the flap covers the loading unit.

The method still further includes the step of positioning the disk over the suture tray such that the loading unit protrudes through tan opening in the disk.

The elongate flap has a panel portion and the method includes folding the elongate flap such that the panel portion of the elongate flap overlies a needle contained within the loading unit when the elongate flap is positioned over the loading unit.

DESCRIPTION OF THE DRAWINGS

Various embodiments of the presently disclosed suture package are disclosed herein with reference to the drawings, wherein:

FIG. 8 is a perspective view of an alternative embodiment of an endostitch package;

FIG. 9 is a perspective view of the endostitch package of FIG. 8 with a package cover removed;

FIG. 11 is a perspective view of another alternative embodiment of an endostitch package;

FIG. 12 is a perspective view of the endostitch package of FIG. 11 with a package cover removed;

DETAILED DESCRIPTION OF EMBODIMENTS

Embodiments of the presently disclosed suture package assemblies, for use with double pointed surgical needles and knotless sutures, will now be described in detail with reference to the drawings wherein like numerals designate identical or corresponding elements in each of the several views. As is common in the art, the term "proximal" refers to that part or component closer to the user or operator, i.e., surgeon or physician, while the term "distal" refers to that part or component further away from the user.

Figure 1:
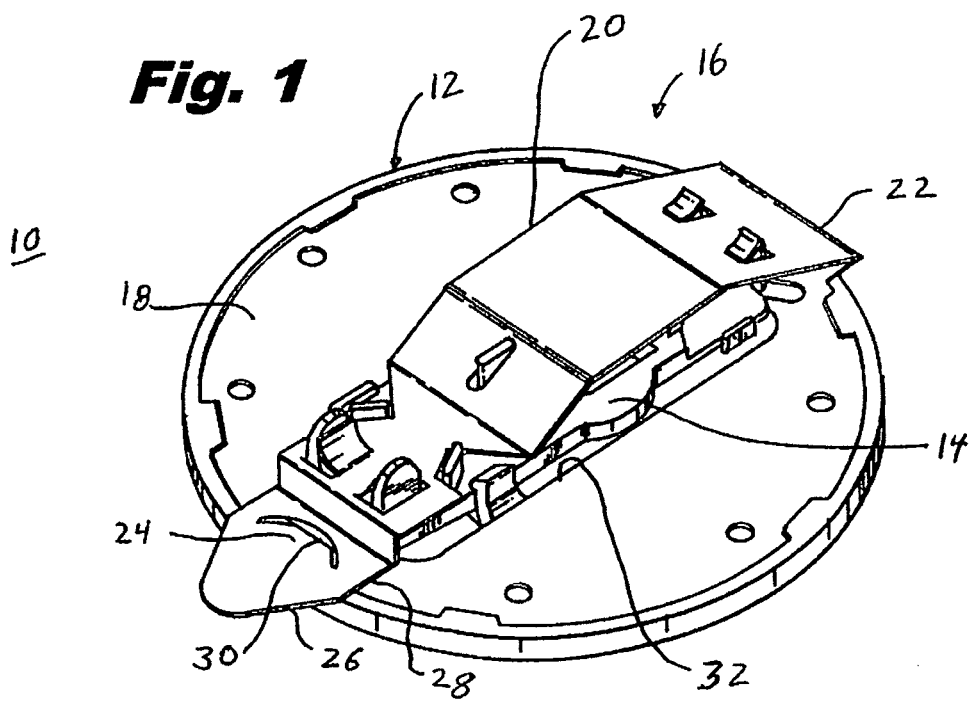
FIG. 1 is a perspective view of one embodiment of an endostitch suture package.

Referring initially to FIG. 1, there is disclosed a suture package assembly 10 for use with a double pointed surgical needle and barbed suture (not shown) as will be described in more detail hereinbelow. Suture package assembly 10 generally includes a circular suture tray 12 having a loading unit 14 mounted upon suture tray 12. Suture tray 12 is provided to retain a length of the barbed suture and a loading unit 14 is provided to support a double pointed surgical needle for presentation to the jaws of the surgical suturing instrument.

In order to retain a length of barbed suture within suture tray 12 as well as protecting a double pointed surgical needle supported within the loading unit 14, suture package assembly 10 further includes a suture package cover 16. Suture package cover 16 includes a circular suture tray cover or disk 18 and a needle or loading unit cover in the form of an elongate flap 20 formed integrally with disk 18. As used herein, the term "disk" refers to that part of the disclosed suture package covers for example suture package cover 16, that is directly affixed to the associated suture tray, for example suture tray 12. Disk 18 and elongate flap 20 are connected along a primary fold line 22.

A tab 24 is formed in a nose 26 located at a distal end 28 of elongate flap 20. Tab 24 is configured to engage a slot 30 foamed within disk 18 in order to secure elongate flap 20 over loading unit 14. A cutout 32 in disk 18 is provided to allow loading unit 14 to project through disk 18.

Figure 2:
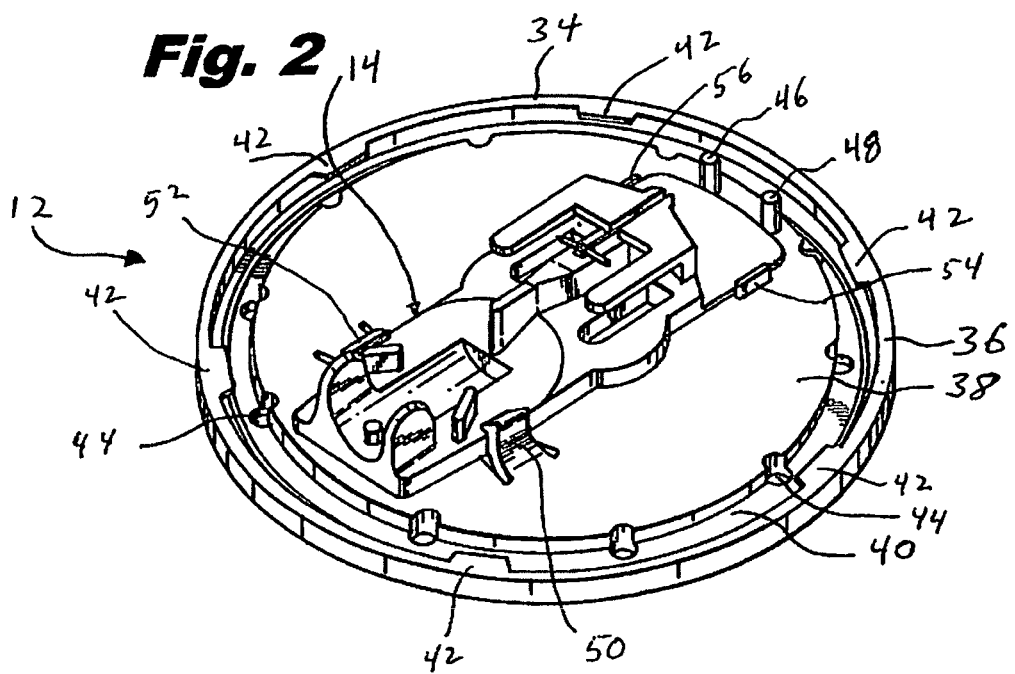
FIG. 2 is a perspective view of the endostitch suture package of FIG. 1 with a package cover removed.

Referring now to FIG. 2, illustrated is a suture tray 12 with the suture tray cover 18 removed. Suture tray 12 generally includes a circular body portion 34 having a peripheral sidewall 36. Body portion 34 includes a raised central portion 38 defining a circular suture trough 40 between peripheral sidewall 36 and raised central portion 38. A plurality of inwardly directed tabs 42 are provided on peripheral sidewall 36 to secure suture package cover 16, and specifically disk 18, to suture tray 12 as best shown in FIG. 1. A plurality of holes 44 extend through body portion 34 between circular suture trough 40 and peripheral sidewall 36 as a result of a molding process to form suture tray 12. Holes 44 may further allow sterilization gases to reach a suture (not shown) positioned within suture trough 40.

Figure 3:
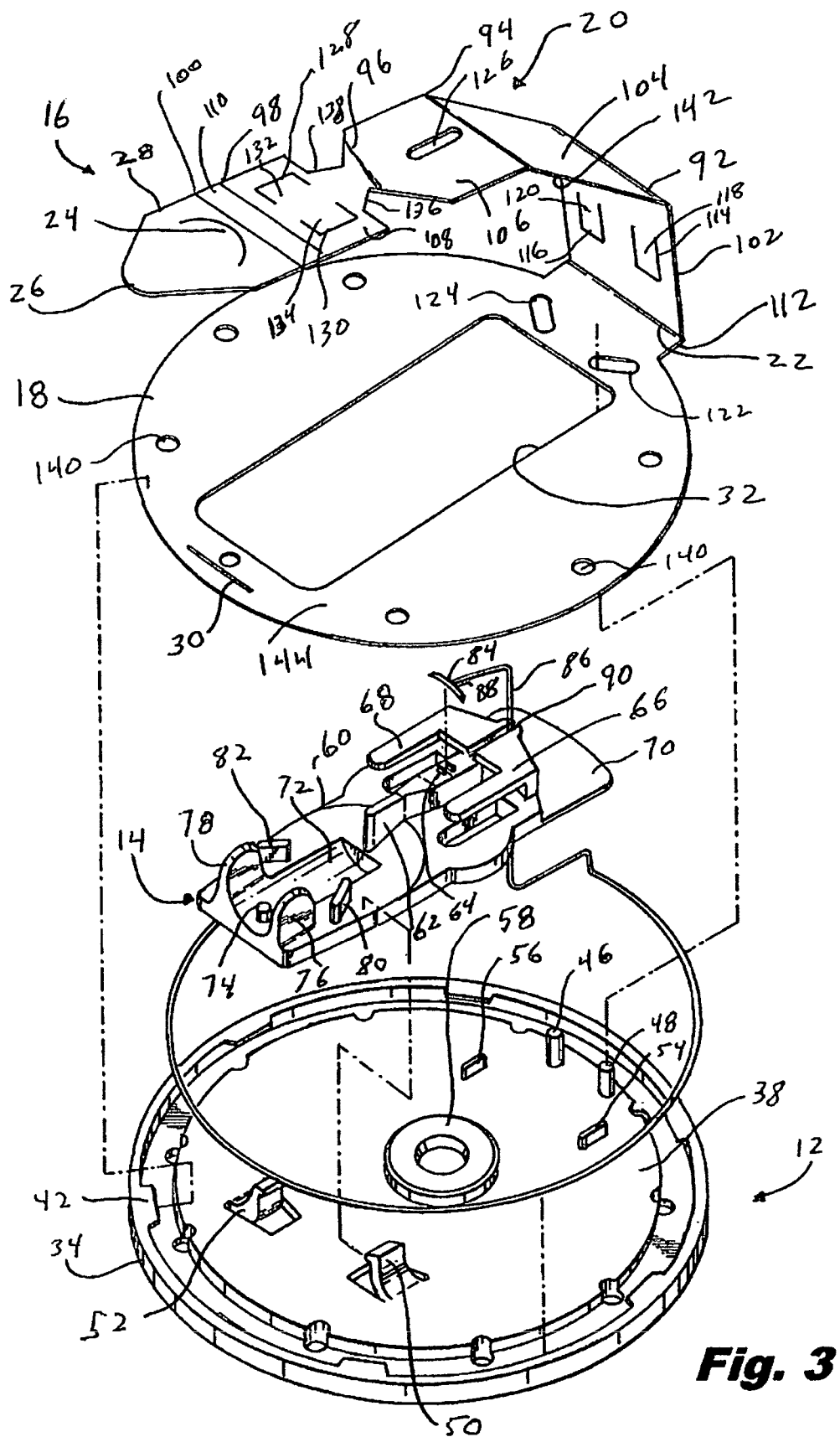
FIG. 3 is an exploded perspective view of the endostitch suture package of FIG. 1 with parts separated.

Referring now to FIGS. 2 and 3, a pair of stop pins 46 and 48 are formed on raised central portion 38 to assist in positioning loading unit 14 on circular body portion 34. Snap hooks 50 and 52, along with alignment tabs 54 and 56, are also provided on raised central portion 38 to properly position and secure loading unit 14 on suture tray 12. A central disc 58 is provided on raised central portion 38 and is configured to engage corresponding structure on loading unit 14. Additionally, where a suture reel (not shown) is associated with loading unit 14, central disc 58 provides support for the suture reel.

As best shown in FIG. 3, loading unit 14 generally includes a base 60 having a needle support member 62 projecting upwardly from base 60. A needle holding notch 64 is provided on needle support member 62 to releasably retain a surgical needle in a manner described in more detail hereinbelow. A pair of upwardly projecting, L-shaped guard arms 66 and 68 are provided adjacent needle support member 62 to properly position jaws of a surgical suturing apparatus about needle support member 62 and prevent removal of the surgical needle until such time as the jaws have been moved to a closed position as described hereinbelow. A fingertip 70 extends from base 60 and is configured to be engaged by stop pins 46 and 48 and alignment tabs 54 and 56, as shown.

An alignment recess 72 is formed within base 60 and is configured to receive a distal end of a surgical suturing instrument. An alignment pin 74 is provided within alignment recess 72 to engage the distal end of the surgical suturing instrument as well as a pair of ears 76 and 78 which are also provided to engage and align the distal end of the surgical suturing instrument. A pair of wings 80 and 82 are also provided on base 60 to facilitate guiding the surgical instrument into alignment with a surgical needle retained within needle support member 62.

As noted hereinabove, loading unit 14 and suture tray 12 are provided to supply a surgical needle, for example double pointed surgical needle 84, along with a length of barbed suture 86, to a surgical suturing apparatus. Length of barbed suture 86 is affixed to double pointed surgical needle 84 at a center 88 of needle 84. A notch 90 is provided between arms 66 and 88 and extends through base 60 to allow length of barbed suture 86 to pass from double pointed surgical needle 84 and into circular suture trough 40 formed in circular body portion 34.

Figure 4:
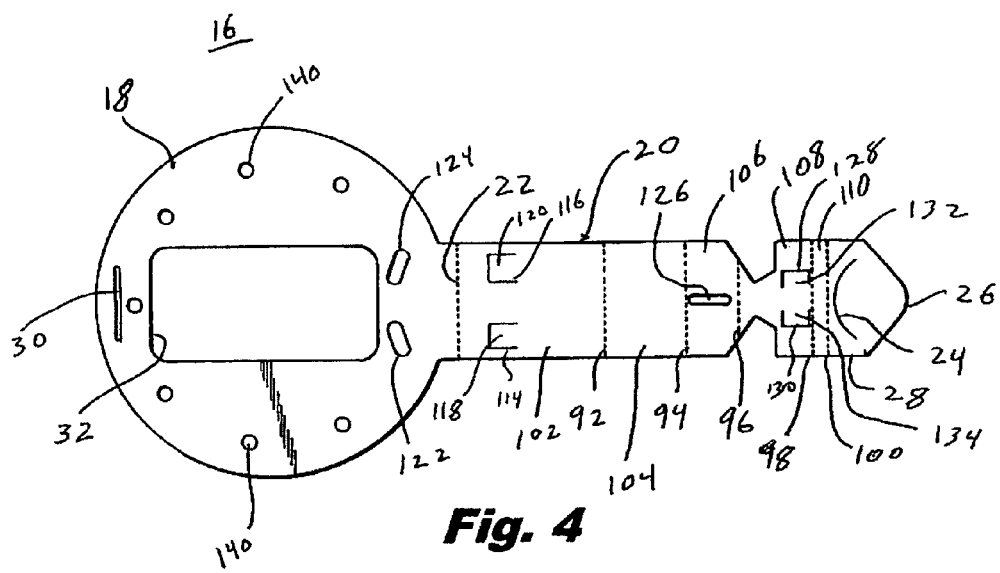
FIG. 4 is a top plan view of the package cover of the endostitch package of FIG. 1.

Referring now to FIGS. 3 and 4, in order to fold elongate flap 20 over loading unit 14, elongate flap 20 includes a plurality of fold lines such as second fold line 92, third fold line 94, fourth fold line 96, fifth fold line 98 and sixth fold line 100. These fold lines, along with primary fold line 22, divide elongate flap 20 into a plurality of panels such as primary panel 102, second panel 104, third panel 106, fourth panel 108 and fifth panel 110. As shown in FIG. 3, a peripheral extension 112 extends from disk 18 to allow primary fold line 22, located between peripheral extension 112 and primary panel 102, to remain straight as primary panel 102 is folded towards disk 18.

In order to accommodate the various features of loading unit 14, elongate flap 20 is provided with a series of cuts or openings. Specifically, primary panel 102 includes a pair of cuts 114 and 116 which form a pair of push out flaps 118 and 120. Push out flaps 118 and 120 cooperate with a pair of cut outs 122 and 124, formed on disk 18, to accommodate stop pins 46 and 48 when disk 18 is positioned on suture tray 12 and elongate flap 20 is folded over loading unit 14. Additionally, an elongate cut out 126 is provided in third panel 106 to provide clearance for needle support member 62. Further, a pair of cut outs 128 and 130 are formed in fourth panel 108 and are provided to accommodate ears 76 and 78 projecting from base 60 of loading unit 14. Finally, fourth panel 108 is provided with a pair of side notches 136 and 138 which are configured to allow room for wings 80 and 82 of loading unit 14. These various cuts, push out flaps and cut outs allow elongate flap 20 to be secured over loading unit 14 by frictional engagement with corresponding structure on loading unit 14.

As shown, disk 18 is additionally provided with a plurality of peripheral holes which cooperate with molding holes 44 formed in circular body portion 34 of suture tray 12 to allow sterilization gases to penetrate suture package assembly 10 and thereby sterilize the disclosed surgical needle and associated length of suture material.

Referring now to FIGS. 3 and 5-7, the assembly and use of suture package assembly 10 will now be described. Initially, loading unit 14 is separated from suture tray 12 and suture package cover 16 is also separated from suture tray 12. Loading unit 14 may be provided in the assembled condition including double pointed surgical needle 84 positioned within needle holding notch 64 on needle support member 62 with a length of barbed suture 86 attached to center 88 of double pointed surgical needle 84. In order to assemble suture package assembly 10, loading unit 14 is manipulated to initially position finger tabs 70 of loading unit 14 against stop pins 46 and 48 projecting from raised central portion 38 of suture tray 12. Loading unit 14 is moved downwardly toward raised central portion 38 to position base 60 of loading unit 14 between alignment tabs 54 and 56 on raised central portion 38. In order to secure loading unit 14 to raised central portion 38, loading unit 14 is pressed down between snap hooks 50 and 52 such that snap hooks 50 and 52 frictionally retain loading unit 14 on raised central portion 38 of suture tray 12.

Thereafter, length of barbed suture 86 is positioned within circular suture trough 40 formed in circular body portion 34 of suture tray 12. Next, disk 18 of suture package cover 16 is advance toward suture tray 12 and loading unit 14. Disk 18 is positioned such that disk 18 is positioned over loading unit 14. Next, disk 18 is manipulated so as to position disk 18 between inwardly directed tabs 42 formed in peripheral sidewall 36 of circular body portion 34 to thereby secure disk 18 to suture tray 12.

Figure 5:
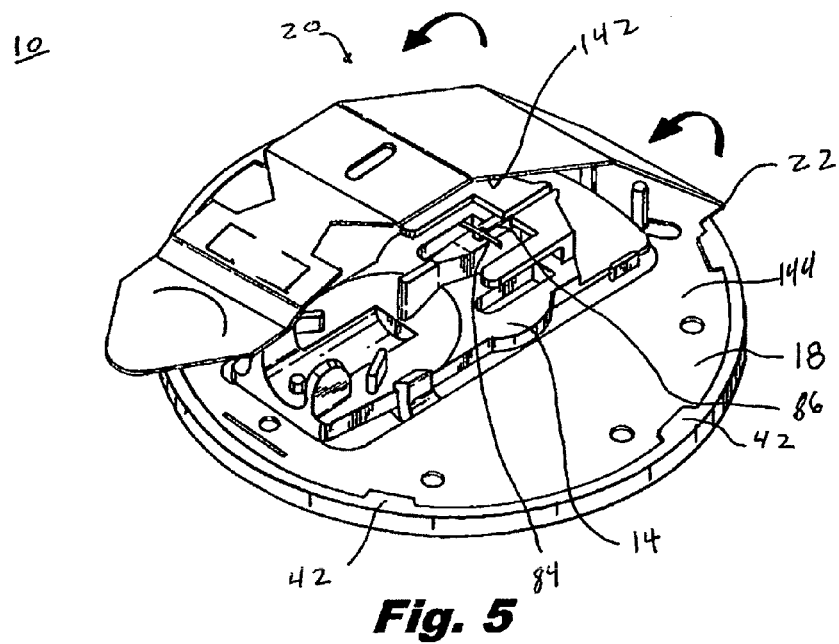
FIG. 5 is a perspective view of the endostitch package of FIG. 1 illustrating an initial folding of a needle cover, of the package cover, over a loading unit.

Referring now to FIG. 5, in order to protect double pointed surgical needle 84 and length of barbed suture 86, located in loading unit 14, elongate flap 20 is initially folded over towards disk 18 along primary fold line 22. This brings a first side 142 of elongate flap 20 into contact with first side 144 of disk 18.

Figure 6:
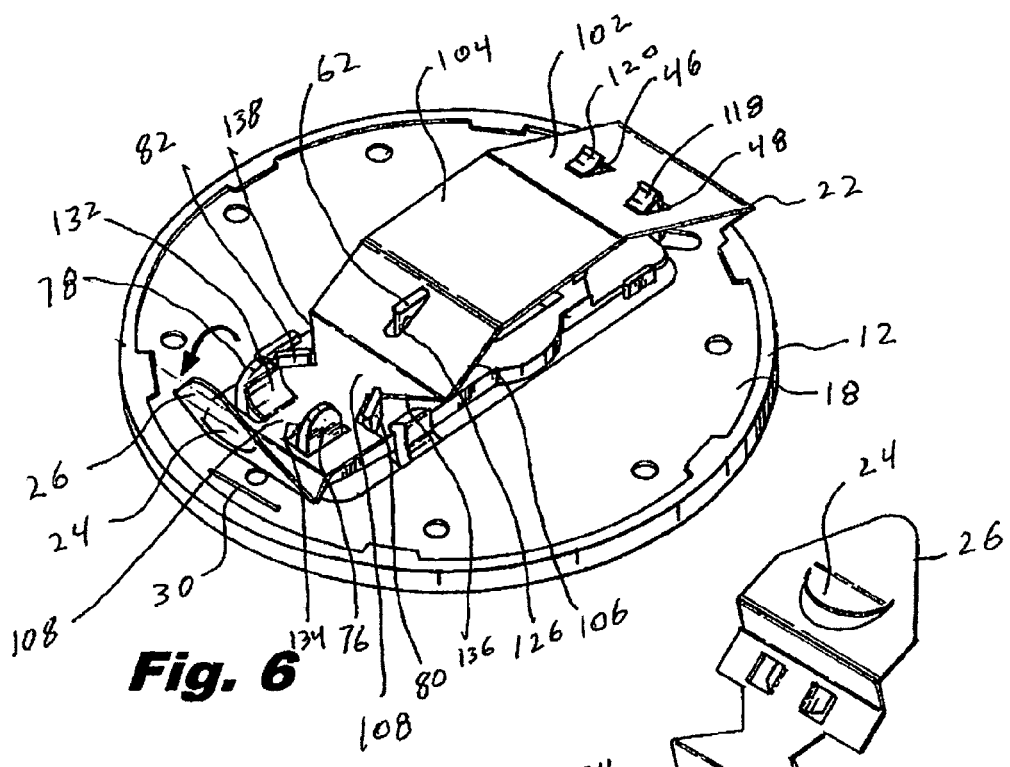
FIG. 6 is a perspective view similar to FIG. 5 illustrating final folding and securement of the needle cover over the loading unit.

With specific reference to FIG. 6, as elongate flap 20 is folded over towards disk 18, stop pins 46 and 48 on suture tray 12 engage and open push-up flaps 120 and 118 formed in primary panel 102. Second panel 104 is positioned over double pointed surgical needle 84 and length of barbed suture 86 (FIG. 5) and third panel is manipulated to position cut out 126 over needle support member 62. At this point, fourth panel 108 is manipulated to position notches 136 and 138 between wings 80 and 82 on loading unit 14. Notches 136 and 138 engage wings 80 and 82 in a friction fit fashion to retain fourth panel 108 relative to loading unit 14. Fourth panel 108 continues to be pressed downwardly relative to loading unit 14 such that ears 76 and 78 force push out flaps 132 and 134 outwardly through cuts 128 and 130 formed in fourth panel 108 (see also FIG. 3).

Finally, nose 26 of elongate flap 20 is manipulated to force tab 24 located in nose 26 into slot 30 located in disk 18 so as to finally secure elongate flap 20 to disk 18. In this manner, loading unit 14 and suture package cover 16 are properly affixed to suture tray 12 to protect double pointed surgical needle 84 and length of barbed suture 86. Thereafter, suture package assembly 10 may be subjected to sterilization processes to prepare double pointed surgical needle 84 and length of barbed suture 86 for use.

Figure 7:
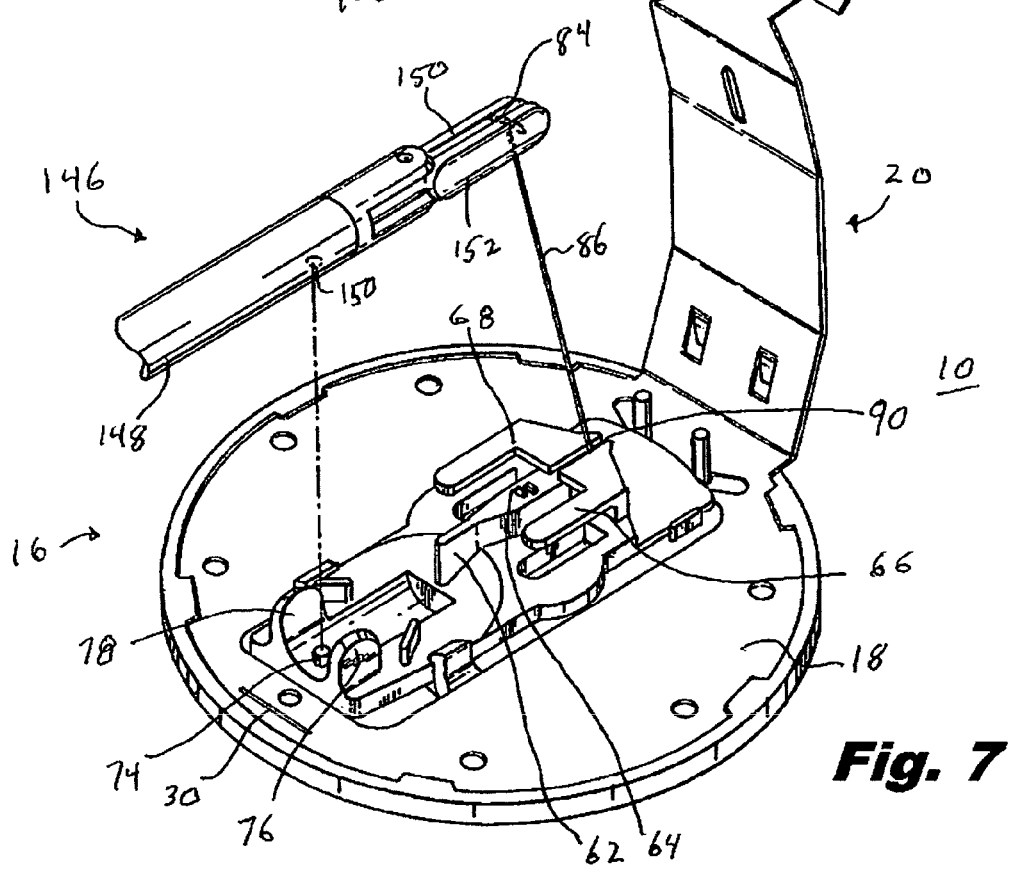
FIG. 7 is a perspective view of the endostitch package of FIG. 1 with the needle cover in an open position and illustrating a surgical instrument removing a surgical needle from the loading unit.

Referring now to FIG. 7, in use, suture package assembly 10 is opened by reversing the procedure described hereinabove with regard to the assembly of suture package cover 16. Specifically, nose 26 of elongate flap 20 is manipulated to draw tab 24 out of engagement with slot 30 formed in disk 18 of suture package cover 16. Elongate flan 20 is then manipulated to pull the various panels and cut outs, previously described, free from loading unit 14. This exposes double pointed surgical needle 84 along with length of barbed suture 86 for use.

A distal end 146 of a surgical suturing apparatus (not shown) is manipulated to position an elongate tubular member 148 of distal end 146 between ears 76 and 78 on loading unit 14. A hole 150 provided on elongate tubular member 148 is positioned over alignment pin 74 in loading unit 14. Thereafter, jaws 150 and 152 are manipulated beneath upwardly projecting L-shaped card arms 66 and 68 so as to surround double pointed surgical needle 84. Double pointed surgical needle 84 and elongate tubular member 148 is lifted free of loading unit 14. As elongate tubular member 148 is lifted free, length of barbed suture 86 is drawn through notch 90 and out of suture package assembly 10. In this manner, suture package assembly 10 protects a double pointed surgical needle 84 and length of barbed suture 86 while supplying them to a surgical instrument for use.

Figure 10:
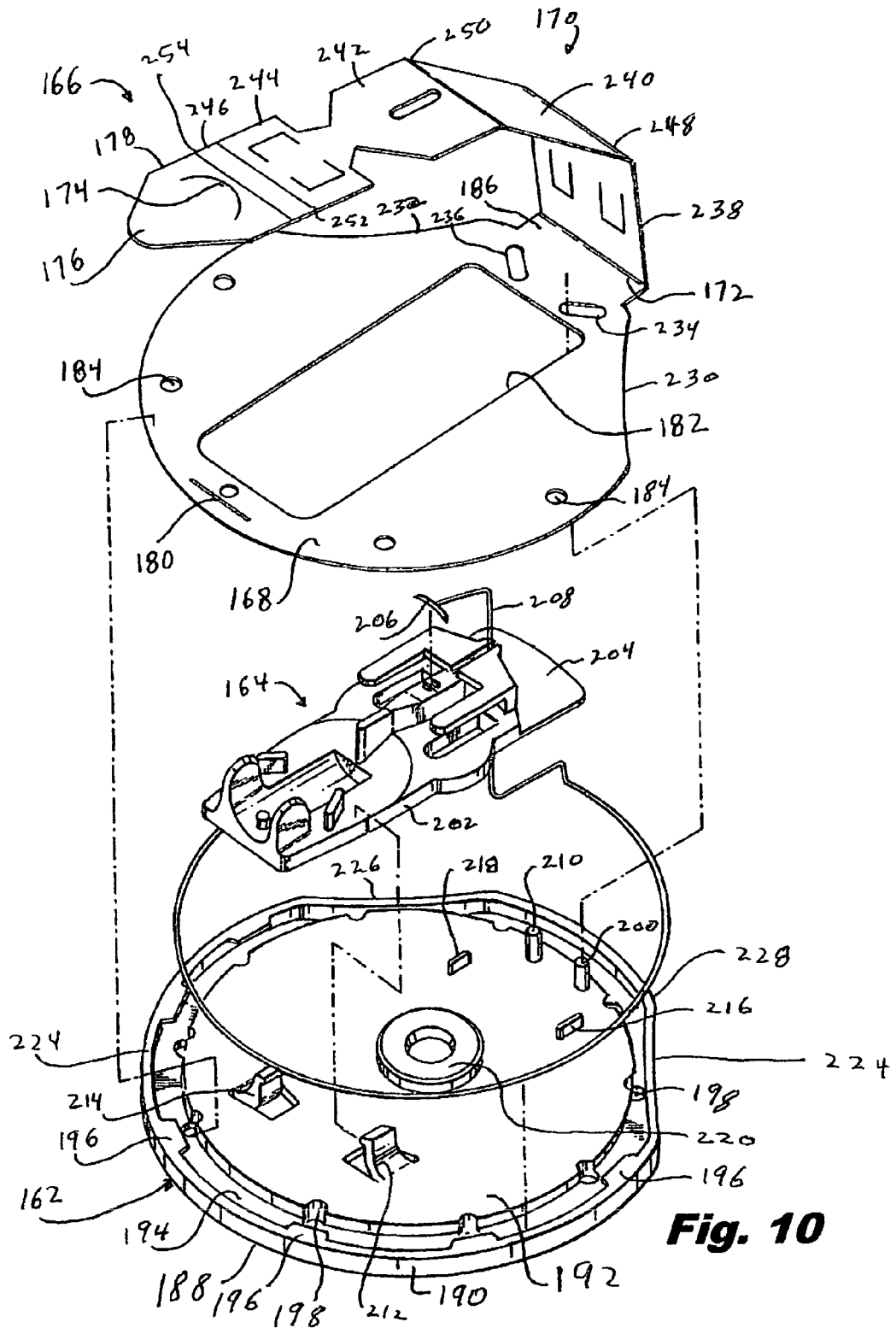
FIG. 10 is a perspective view of the endostitch package of FIG. 8 with parts separated.

Referring now to FIGS. 8-10 there is disclosed an alternative embodiment of a suture package assembly 160 for use with a surgical suturing apparatus. Suture package assembly 160 generally includes a suture tray 162 having a loading unit 164 mounted thereon. A suture package cover 166 is provided to protect the contents of suture tray 162 as well as protecting loading unit 164. Suture package cover 166 generally includes a disk 168 having an elongate flap 170 extending from disk 168. Elongate flap 170 is connected to disk 168 along a primary fold line 172. Elongate flap 170 is secured over disk 168 by engagement of a tab 174, formed in a nose panel 176 at a distal end 178 of elongate flap 170, with a slot 180 formed in disk 168. Similar to disk 18 described hereinabove, disk 168 includes a cut out 182 for passage of loading unit 164 therethrough.

Disk 168 also includes a plurality of peripheral holes 184 which may facilitate the sterilization of the contents of suture package assembly 160. Disk 168 further includes a tab 186 extending from this 168 to primary fold line 172.

Referring now to FIG. 9, suture tray 162 generally includes a body portion 188 having a peripheral sidewall 190. Body portion 188 includes a raised central portion 192 defining a suture trough 194 between peripheral sidewall 190 and raised central portion 192. A plurality of inwardly directed tabs 196 are provided on peripheral sidewall 190 to secure suture package cover 162, and specifically disk 168, to suture tray 162 as best shown in FIG. 8. A plurality of holes 198 extend through body portion 188 between suture trough 194 and peripheral sidewall 190 as a result of a molding process utilized to form suture tray 162. Holes 198 may further allow sterilization gases to reach a suture (not shown) positioned within suture trough 194.

Referring now to FIGS. 9 and 10, a pair of stop pins 200 and 210 are formed on raised central portion 192 to assist in positioning loading unit 164 on body portion 188. Snap hooks 212 and 214, along with alignment tabs 216 and 218, are also provided on raised central portion 192 to properly position and secure loading unit 164 on suture tray 162. A central disk 220 is provided on raised central portion 192 and is configured to engage corresponding structure on loading unit 164. Additionally, where a suture reel (not shown) is associated with loading unit 164, central disk 220 provides support for the suture reel.

Loading unit 164 is identical to loading unit 14 described hereinabove and generally includes a base 202 having a tab 204 extending from base 202. Similar to that described hereinabove, tab 204 is positioned adjacent stop pins 200 and 210 and between alignment tabs 216 and 218. Loading unit 164 is held in place on raised central portion 192 by engagement with snap hooks 212 and 214 with base 202 of loading unit 164. Suture package assembly 160 additionally includes a double pointed surgical needle 206 having a length of barbed suture 208 extending from needle 206.

Referring specifically to FIGS. 9 and 10, suture tray 162 is ergonomically designed to facilitate handling by the user. Specifically, peripheral sidewall 190 includes a circular peripheral portion 222 and a pair of recessed or scalloped peripheral portions 224 and 226. Scalloped peripheral portions 224 and 226 provide recessed areas capable of easily being grasped by the fingers of the user. A tab peripheral portion 228 is provided intermediate scalloped peripheral portions 224 and 226. Similarly, with reference to FIGS. 8 and 10, disk 168 is provided with a pair of recessed or scalloped portions 230 and 232 separated by tab 186. As shown, disk 168 additionally includes a pair of slots 234 and 236 to provide clearance for stop pins 200 and 210 when disk 168 is affixed to suture tray 162.

With specific reference to FIG. 10, elongate flap 170 is identical to elongate flap 20 described hereinabove with respect to suture package assembly 10. Specifically, elongate flap 170 includes a primary panel 238, a secondary panel 240, a third panel 242, a fourth panel 244 and a fifth panel 246. The disclosed panels are separated by a second fold line 248, a third fold 250, a fourth fold line 252 and a fifth fold line 254. Finally, elongate flap 170 includes punch outs and slots identical to those provided in elongate flap 20 to accommodate the various features of loading unit 164.

Figure 13:
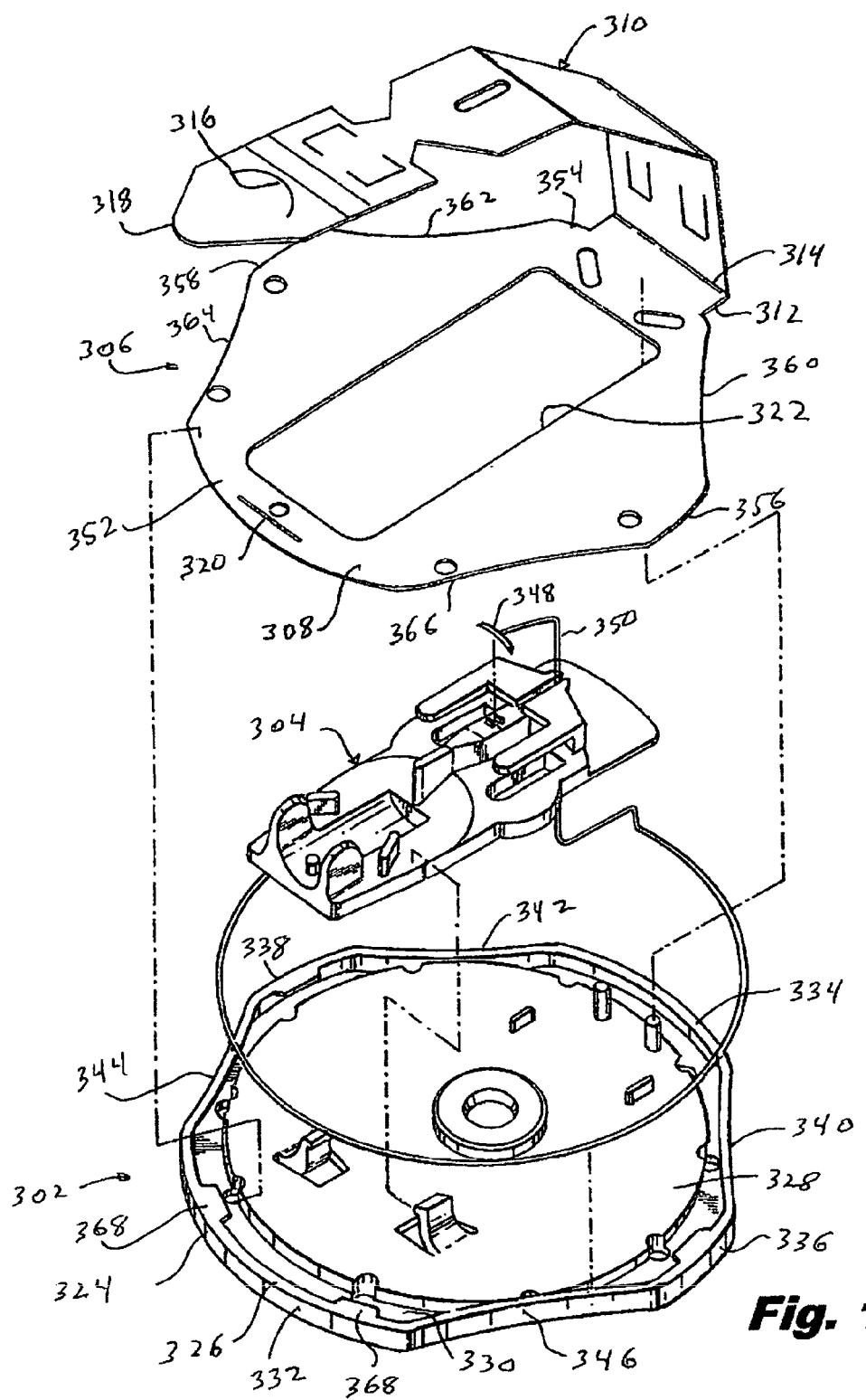
FIG. 13 is a perspective view of the endostitch package of FIG. 11 with parts separated.

Referring now to FIGS. 11-13, there is disclosed a further alternative embodiment of a suture package assembly 300. With initial reference to FIG. 11, and similar to those embodiments described hereinabove, suture package assembly 300 generally includes a suture tray 302 having a loading unit 304 removably affixed to suture tray 302. Loading unit 304 is identical to the loading units previously described hereinabove and includes all the features and functions disclosed above. A suture package cover 306 is provided to protect a needle and suture assembly (not shown) contained within suture package assembly 300. Suture package cover 306 includes a disk 308 having an elongate flap 310 extending from disk 308. Elongate flap 310 is connected to disk 308 at a tab portion 312 of this 308 along a primary fold line 314. Identical to those embodiments described hereinabove, a tab 316 is provided in a nose panel 318 of elongate flap 310 and is configured to engage a slot 316 in disk 308 to retain elongate flap 310 in a closed position over loading unit 304. The remaining features of elongate flap 310 are identical to those features, including panels, fold lines, cut outs and slots described hereinabove with regard to elongate flap 20 in suture package assembly 10.

Referring now to FIGS. 12 and 13, suture tray 302 includes a body portion 324 having a peripheral rim 326 and a raised central portion 328 defining a suture trough 330 therebetween. Suture tray 302 is also ergonomically designed to facilitate grasping by the hand of a user. Specifically, peripheral rim 326 includes a distal arcuate portion 332 and a proximal or tabbed arcuate portion 334. Tabbed arcuate portion 334 corresponds to the position of tab 312 extending from disk 308 adjacent primary fold line 314 of suture package cover 306. Peripheral rim 326 additionally includes side arcuate portions 336 and 338. In order to facilitate grasping by the hand of a user, peripheral rim 326 additionally includes a plurality of recessed or scalloped portions 340, 342, 344 and 346 located intermediate respective distal arcuate portion 332, tabbed arcuate portion 334 and side arcuate portions 336 and 338.

Finally, suture package assembly 300 additionally includes a double pointed surgical needle 348 mounted on loading unit 304 in a manner identical to that described hereinabove with regard to previous double pointed surgical needles of loading units. A length of barbed suture material 350 extends from double pointed surgical needle 348, through loading unit 304, and is retained within suture trough 330 formed in body portion 324 of suture tray 302.

Likewise, with reference back to FIG. 13, disk 308 includes corresponding distal arcuate portion 352, proximal or tabbed arcuate portion 354 located adjacent tab 312 and side arcuate portions 356 and 358 which correspond to distal arcuate portion 332, tabbed arcuate portion 334 and side arcuate portions 336 and 338 of peripheral rim 326 on suture tray 302. Disk 308 additionally includes recessed or scalloped portions 360, 362, 364 and 366 corresponding to scalloped portions 340, 342, 344 and 346 of peripheral rim 326. Finally, a plurality of tabs 368 are provided on peripheral rim 326 to retain disk 308 in position on tray 302.

Figure 14:
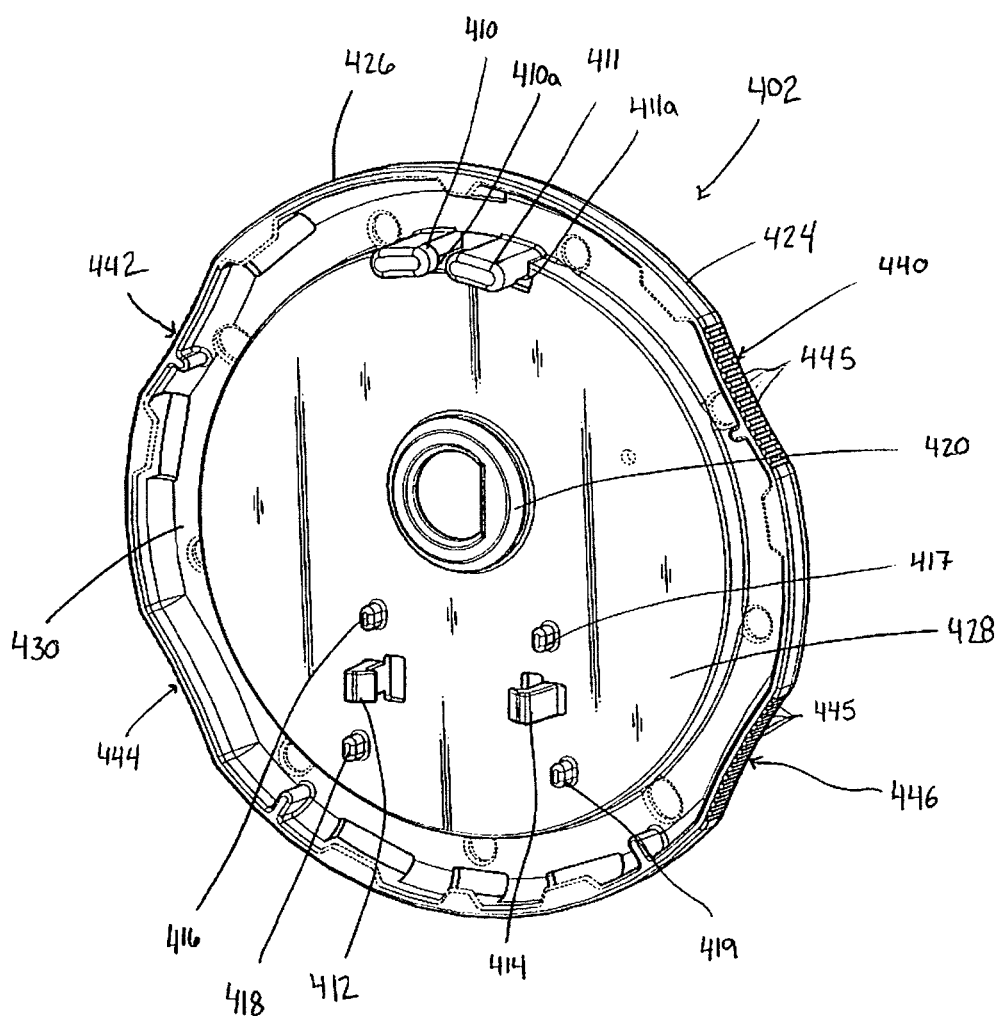
FIG. 14 is a perspective view of a suture tray of yet another embodiment of a endostitch package.

With reference now to FIG. 14, disclosed is a suture tray 402 from yet another embodiment of a suture package assembly. Suture tray 402 is substantially similar to suture tray 302, and therefore will be described only as relates to the differences therebetween. Suture tray 402 includes a body portion 424 having a peripheral rim 426 and a raised central portion 428 defining a suture trough 430 therebetween. Suture tray 402 is ergonomically designed to facilitate grasping by the hand of a user. Specifically, peripheral rim 426 includes a plurality of recessed or scalloped portions 440, 442, 444, 446, each of which may include ridges, nubs or other suitable texture 445.

Still referring to FIG. 14, a pair of stop tabs 410, 411 each including a notch 410a, 411a, respectively, are formed on raised central portion 428 to assist in positioning loading unit 304 (FIG. 16) on body portion 424. Specifically, notches 410a, 411a are configured to receive a portion of the base of loading unit 304. Snap hooks 412, 414, along with alignment tabs 416, 417, 418, 419 are also provided on raised central portion 428 to properly position and secure loading unit 304 on suture tray 402. A central disk 420 is provided on raised central portion 428 and is configured to engage corresponding structure on loading unit 304. Additionally, where a suture reel (not shown) is associated with loading unit 304, central disk 420 provides support for the suture reel.

Figure 15:
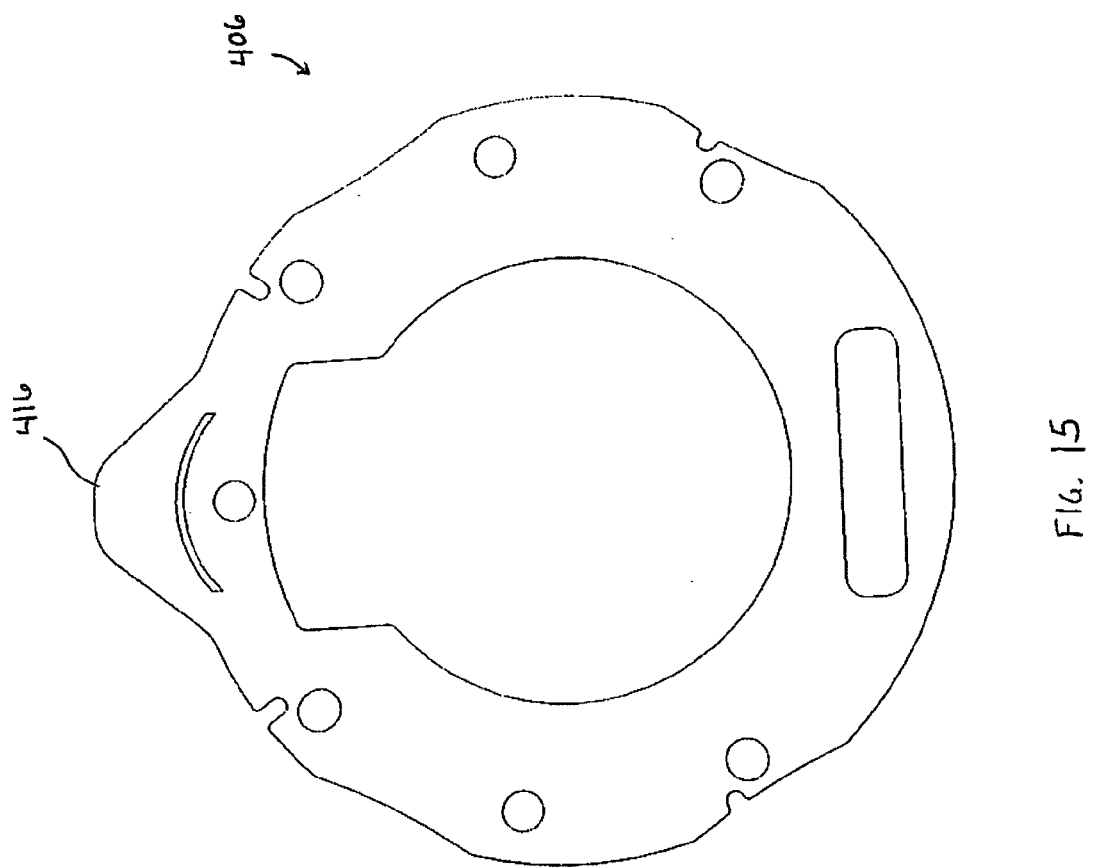
FIG. 15 is an enlarged top view of a cover configured to engage the suture tray of the endostitch package of FIG. 14; and, FIG. 16 is a perspective view of the suture tray of FIG. 14 including the cover of FIG. 15 and the loading unit of FIG. 13.

Turning now to FIG. 15, shown is a suture package cover 406 configured to engage suture tray 402. Suture package cover 406 is substantially similar to suture package cover 306 (FIG. 13) described hereinabove. Suture package cover 306 includes a disk 308 and a tab 416 extending radially outward from disk 308 for facilitating removal of suture package cover 406 from suture tray 402.

Figure 16:
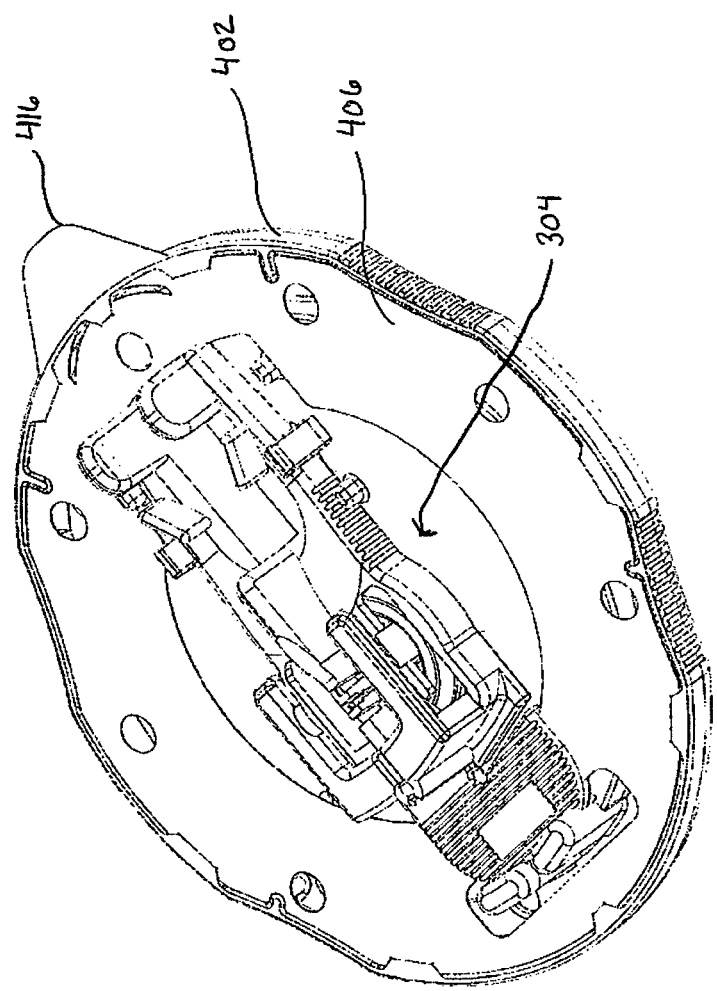

With reference now to FIG. 16, suture tray 402 is shown including positioning loading unit 304 mounted thereon. Suture package cover 406 is configured to be received about positioning loading unit 304 and selectively to engage suture tray 402.

It will be understood that various modifications may be made to the embodiments disclosed herein. For example, the recessed or scalloped portions of the disclosed suture trays may be ribbed or otherwise textured to facilitate grasping by the hand of a user. Further, the disclosed suture package assembly may be mated to a second suture package assembly to provide multiple needle-suture assemblies in a single suture package. Therefore, the above description should not be construed as limiting, but merely as exemplifications of particular embodiments. Those skilled in the art will envision other modifications within the scope and spirit of the claims appended hereto.

The invention claimed is:

1. A suture package comprising:
    a suture tray including a rim and a central body portion, the suture tray defining a suture retaining portion between the rim and the central body portion; and
    a loading unit engaged with the central body portion of the suture tray, wherein the central body portion of the suture tray includes at least one tab defining a notch for receiving a portion of the loading unit, at least one pair of alignment members for aligning the loading unit with the central body portion, and at least one pair of retaining members for engaging the loading unit and maintaining the loading unit in position relative to the central body portion; and
    a cover selectively securable to the suture tray and defining a cutout. wherein the loading unit is received through the cutout when the cover is secured to the suture tray.

2. The suture package according to claim 1, wherein the cover encloses the suture retaining portion when the cover is secured to the suture tray.

3. The suture package according to claim 2, wherein at least a portion of the cover is disposed between the loading unit and the suture tray.

4. The suture package according to claim 2, wherein the suture tray includes a plurality of inwardly directed tabs along the rim.

5. The suture package according to claim 4, wherein the cover is configured for selective engagement within the plurality of inwardly directed tabs.

6. The suture package according to claim 2, wherein the rim includes at least a first scalloped portion configured to facilitate grasping of the suture tray by a user.

7. The suture package according to claim 6, wherein the cover includes at least a first recess corresponding to the at least first scalloped portion of the rim.

8. The suture package according to claim 2, wherein the cover includes at least one notch configured to engage at least one inwardly extending protrusion formed on the rim.

9. The suture package according to claim 2, wherein the suture tray defines a plurality of openings in the suture retaining portion.

10. The suture package according to claim 9, wherein the cover defines a plurality of openings corresponding to the plurality of openings in the circumferential suture retaining portion.

11. The suture package according to claim 2, wherein the cover further includes a flange configured to facilitate separation of the cover from the suture tray.

12. The suture package according to claim 1, further including a suture, wherein at least a portion of the suture is received within the suture retaining portion.

13. The suture package according to claim 12, wherein the suture is barbed.

14. The suture package according to claim 12, wherein the suture includes a double pointed surgical needle.

15. The suture package according to claim 14, wherein the loading unit is configured to engage the double pointed surgical needle.

16. The suture package according to claim 1, wherein the loading unit includes a support for maintaining a needle above a topmost surface of the rim.

* * * * *